United States Patent [19]

Lacey

[11] Patent Number: 4,484,769
[45] Date of Patent: Nov. 27, 1984

[54] NON-RIGID UNIVERSAL COUPLING FOR HEALTH RELATED EQUIPMENT

[75] Inventor: William J. Lacey, Northport, N.Y.
[73] Assignee: Hospitak, Inc., Lindenhurst, N.Y.
[21] Appl. No.: 446,662
[22] Filed: Mar. 9, 1983
[51] Int. Cl.³ .............................................. F16L 25/00
[52] U.S. Cl. ....................................... 285/12; 285/331; 285/110; 285/423; 285/239; 285/DIG. 22
[58] Field of Search .................. 285/12, 331, 110, 423, 285/238, 239, DIG. 22

[56] References Cited

U.S. PATENT DOCUMENTS 3,680,896  8/1972  Cupit ................................. 285/423 X
3,768,476  10/1973  Raitto ............................. 285/331 X
3,976,311  8/1976  Spendlove ........................... 285/12
3,997,195  12/1976  Bartholomew ................. 285/331 X
4,022,205  5/1977  Tenczar .......................... 285/423 X Primary Examiner—Richard J. Scanlan, Jr.
Attorney, Agent, or Firm—Eisenman, Allsopp & Strack

[57] ABSTRACT

An expendable adaptor for quick coupling flexible hoses to a variety of devices such as oxygen breathing equipment and including an enlarged deformable head portion having at least a pair of concentric sleeves the inner of which is axially recessed so that its forward face engages an end edge of a complementary coupling fitting in sealing relationship while the outer sleeve surrounds the fitting in a secondary sealing as well as anchoring relationship.

7 Claims, 4 Drawing Figures

NON-RIGID UNIVERSAL COUPLING FOR HEALTH RELATED EQUIPMENT

BACKGROUND OF THE INVENTION

This invention relates to coupling adaptors for joining tubing to various sources and devices particularly health related devices such as oxygen breathing equipment, hand held nebulizers and the like in which the tubing and coupling adaptors are disposable.

Disposable flexible tubing has found almost universal acceptance in health related devices such as oxygen breathing equipment using cannulas, masks or tents, hand held nebulizers, humidifiers, air entrainment oxygen diluters, ambu bags and the like. The tubing comes typically as a disposable product, the cost of which is lower than the expense of reprocessing reusable tubing. A weak link in this otherwise efficient medical procedure is the coupling fitting or adaptor for joining the tubing to the basic equipment, such for example as the flow meter/pressure regulator attached to an oxygen cylinder. Such fittings have heretofore been made of relatively expensive parts which are easily lost as well as cumbersome to use.

The present invention has for its objectives to provide a coupling fitting or adaptor which is so inexpensive as to be disposable along with the tubing and which at the same time is simpler to use, consuming a fraction of the time necessary to complete conventional coupling.

In accordance with one embodiment of the invention, the coupling adaptor is formed with a compound front end structure including an outer cylindrical sleeve and recessed axially therein a secondary cylindrical sleeve the central opening of which corresponds to the inside diameter of the tubing. The inner and outer sleeves are spaced apart radially to form a toroidal space at the inner end of which the two sleeves are joined. The adaptor is formed of a relatively deformable material so that it can flex and deform as necessary to be slid over for example a standard output fitting of an oxygen flow meter with a primary seal being formed by the axial engagement of the inner sleeve with the forward wall of the standard fitting and with the outside sleeve snugly stretched over the outside surface to form a secondary seal as well as a tight gripping action which holds the coupling in place.

Figure 1:
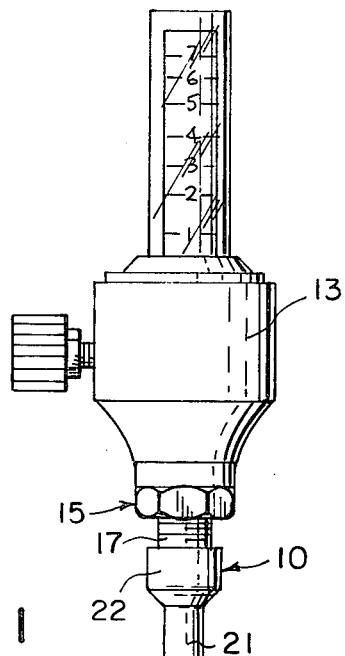
FIG. 1 shows a health related device in the form of an oxygen source having a flow meter/pressure regulator connected by a flexible tube and disposable coupling to a cannula.
Figure 3:
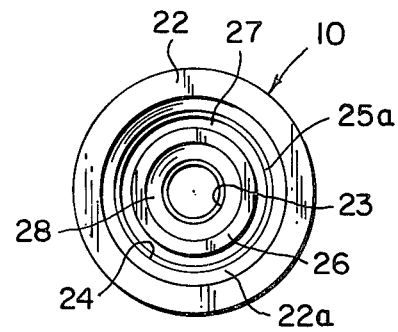
FIG. 3 is a view in end elevation of the forward end of the coupling adaptor.

Referring to the drawings, the invention is illustrated as embodied in a disposable coupling fitting 10 and flexible tubing 11 joining oxygen cannula 12 (adapted to be fitted into the nostrils of a patient) to a conventional flow meter and pressure regulator assembly 13 attached to an oxygen source (not shown) which can take the form of a conventional oxygen cylinder or a pipe from a central source. The flow meter has a standard conventional output fitting 15 to which the coupling adaptor 10 is attached.

Figure 2:
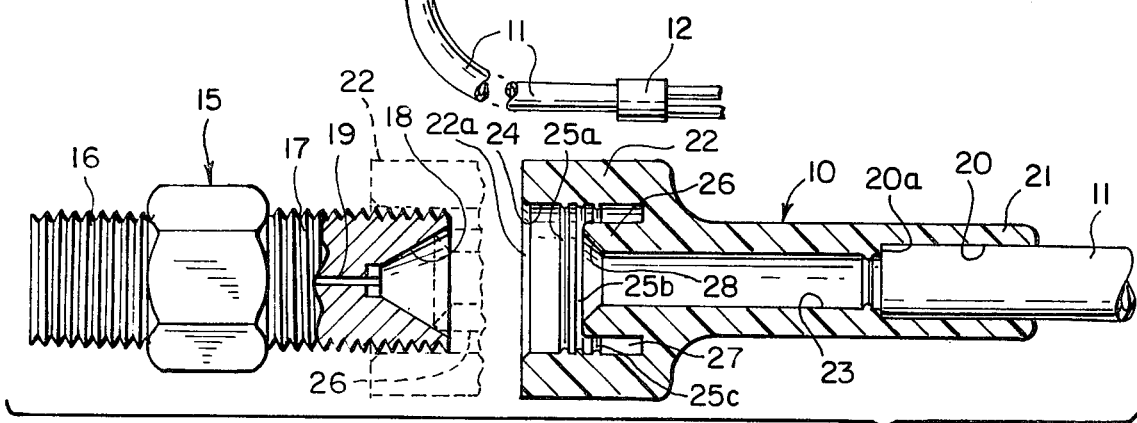
FIG. 2 is a view in enlarged scale showing the disposable coupling adaptor in longitudinal cross section in position to be coupled to the output fixture of the flow meter. Shown in broken lines is the coupling adaptor mated with the fixture.

Referring to FIG. 2, the coupling adaptor 15 includes a threaded shank 16 which is joined to the housing of the flow meter and an output fitting 17 in the form of a threaded shank having a conically recessed forward face 18 at the apex of which is the oxygen duct 19. The tubing 11 is connected to the adaptor fitting 10 by insertion into a cylindrical opening 20 in the tail piece 21. The fit between the tubing and opening is typically a snug fit made permanent by means of an adhesive bond achieved in most cases by the application of a solvent for the materials of which the two members are formed. The fully home position of the tube in the coupling adaptor is defined by an internal shoulder 20a. The forward portion of the coupling includes an enlarged cylindrical head portion 22 coaxial with respect to a duct 23 which connects coaxially to the tube 11 and its cylindrical mounting hole 20.

The head portion 22 includes an enlarged coaxial cylindrical opening 24, the wall of which is formed with a plurality of raised ribs 25a, 25b, 25c. Extending forwardly and coaxially within the opening 24 is an internal sleeve 26 which is spaced from the inside wall of the opening 24 to define a toroidal space 27. The forward end of the sleeve 26 is formed with an outward flare 28 and its forward face terminates approximately half way between the first and last rib 25a and 25c. The forward face of the sleeve 26, the ribs 25a, b, c, and the forward face of the outer cylindrical portion 22 are all contained in planes perpendicular to the axis of the fitting.

The fitting as illustrated is formed as one integral unit and in accordance with the invention is deformable. In one embodiment of the invention the coupling was formed of polyvinyl chloride having a hardness rating of 70 durometers although a range of 40 to 85 durometers has been found to be operative. Thermoplastic rubbers can also be used over a similar range of hardnesses. A coupling adaptor to mate with the fitting 15 of the pressure regulator 13 is sized so that the head portion 22 of the coupling is deformed in tension as it is pressed over the threaded output fitting 17. A typical diameter for the output fitting 17 is 0.560 inches. To assure deforming of the head portion 22, the inside diameter is dimensioned in the range of 0.500 inches. The wall of the outer cylindrical portion is made relatively thick, on the order of 0.140 of an inch, although a range of thicknesses from 0.100 to 0.240 inches can be used. The forward end of the head portion is formed with a bevel 22a to facilitate the coupling in which the adaptor 10 is simply pushed or slid onto the fitting 17 until the forward end of the inner sleeve 26 abuts against the conical recess 18 (as shown in broken lines in FIG. 2), thus deforming slightly the material of which the sleeve is formed to make a first seal. The outer cylindrical portion 22 is deformed or stretched radially outwardly. The ribs 25a–c further deform into the roots of the threads thus strengthening the grip of the push or slide fit.

Figure 4:
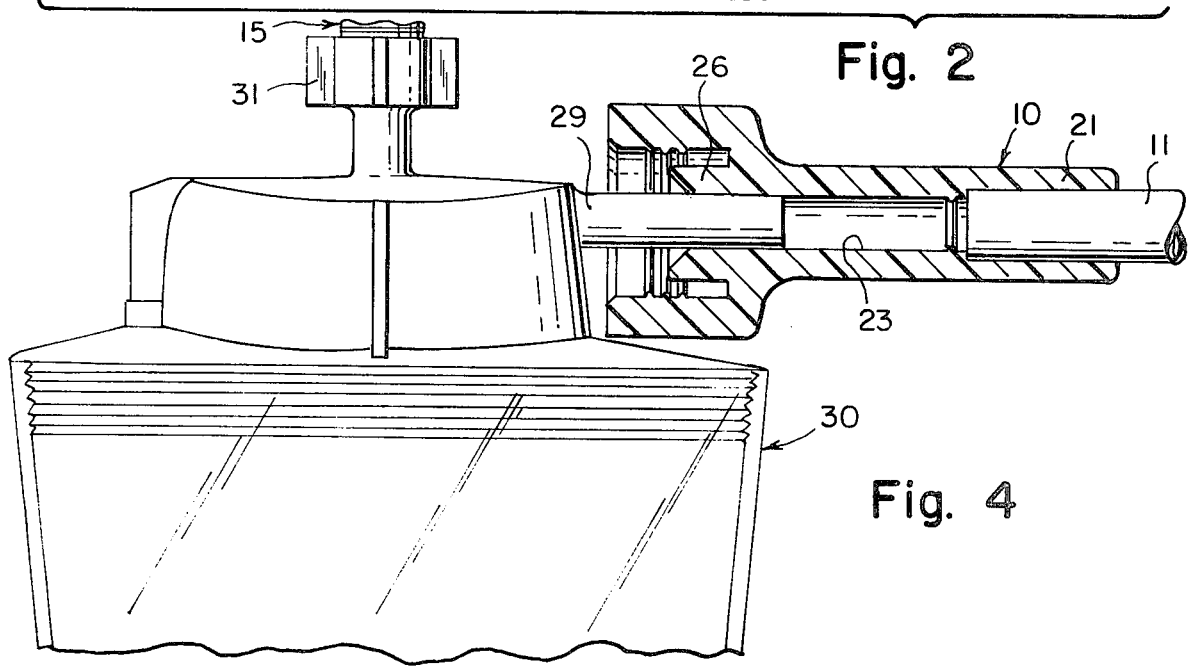
FIG. 4 is a view in longitudinal cross section showing the coupling adaptor mated with a standard output fitting of a humidifier for an oxygen breathing system.

Referring to FIG. 4, the coupling adaptor 10 is shown joined to a standard output fitting 29 of the type normally furnished with humidifiers for use for oxygen breathing systems. The humidifier includes a conventional internally threaded coupling 31 at its top which is screwed into the threaded fitting 15 of the oxygen source to direct the stream of oxygen to a water reservoir to entrain water vapor, after which the humidified oxygen passes through the output fitting 29. The fitting 29 is in the form of a nozzle which is received snugly within the inner sleeve 26 of the adaptor. To this end the inner sleeve has an inside diameter of approximately 0.192 inches, with a taper 28 formed on its inner wall to receive the nozzle. The fit is tight and is accommodated by the resilience of the material of which the coupling 10 and its inner sleeve 26 are molded. The output fitting 29 is typically tapered to insure a snug fit.

While the invention has been described having reference to a preferred embodiment, it will be understood that it can take various other forms and should not therefore be limited except as set forth in the following claims.

I claim:

1. A universal adaptor for selectively coupling flexible tubing to equipment having male fittings of at least two different outside diameters, the larger of which has a threaded exterior surface, the invention comprising:
   a body portion having an inner end apertured to receive a flexible tube;
   an enlarged outer end having a soft radially outwardly deformable hollow section having substantially cylindrical inside diameter to grip the exterior threaded surface of the male fitting thereof to establish resistance against axial movement; and
   a coaxial inner hollow substantially cylindrical section integral with the outer section and formed of relatively soft deformable material having a hardness rating in the range of 40 to 85 durometers, the forward end of the inner section being contained in a plane perpendicular to the axis of the outer cylindrical section and recessed with respect to the forward end of the outer section and adapted to be engaged by a forwardly facing portion of the larger male fitting to deform when engaged thereby to form a seal therewith which is maintained by the resistance against axial movement of the adaptor on the fitting as established by the outer section, said inner section having an inside diameter slightly smaller than the outside diameter of the smaller male fitting and adapted to be entered by the smaller male fitting to deform radially outwardly in sealing relationship therewith.

2. A universal adaptor as set forth in claim 1 including a plurality of raised ribs formed on the inner surface of the outer cylindrical section.

3. The universal adaptor as set forth in claim 2, said ribs being disposed both forwardly and rearwardly of the forward end of the inner cylindrical section.

4. A universal adaptor as set forth in claim 1, said adaptor being formed as a single integrated member.

5. A universal adaptor as set forth in claim 1, the forward end of the inner cylindrical section having an inwardly tapering recess merging with a through bore extending coaxially through the body portion.

6. A universal adaptor as set forth in claim 1, said body portion being selected from among polyvinyl chloride and thermoplastic rubber.

7. A coupling for joining conduits carrying fluid materials comprising
   a relatively rigid male fitting having a threaded cylindrical exterior surface and a relatively small central duct, the forward end of the fitting having a narrow circular edge contained in a plane perpendicular to the axis of the cylindrical surface and
   a radially inwardly converging conical wall defining a forwardly facing recess connecting the circular edge and the central duct,
   and a mating female fitting adapted to receive the male fitting comprising
   a body portion having one end adapted to be coupled to a fluid conduit,
   an enlarged forward end adapted to engage the exterior threaded surface of the male fitting to establish resistance against relative axial movement and
   a coaxial hollow inner cylindrical section defining a portion of the fluid passage through the fitting and formed of relatively soft deformable material integral with the outer section, the inner cylindrical surface of the outer section, and the outer cylindrical surface of the inner section being spaced apart to define a toroidal space to receive the narrow circular forward edge of the male fitting, the forward edge of the inner section being contained in a plane perpendicular to the central axis of the fitting and recessed with respect to the forward end of the outer section and adapted to be engaged and deformed in sealing relationship by the conical wall of the male fitting, which seal is maintained by the resistance against relative axial movement between the fittings.

* * * * *